United States Patent
Gueret

[11] Patent Number: 5,180,240
[45] Date of Patent: Jan. 19, 1993

[54] PROCESS FOR COMPACTING A PULVERULENT MIXTURE ON A SUPPORT AND MAKE-UP APPLICATOR FORMED BY A SUPPORT PROVIDED WITH A PELLET OF COMPACTED PULVERULENT MIXTURE

[75] Inventor: Jean-Louis H. Gueret, Paris, France

[73] Assignee: L'Oreal, Paris, France

[21] Appl. No.: 872,042

[22] Filed: Apr. 22, 1992

[30] Foreign Application Priority Data

Apr. 29, 1991 [FR] France ............................ 91 05244

[51] Int. Cl.$^5$ .................... A45D 33/38; A45D 40/20; B65B 1/22; B30B 11/04
[52] U.S. Cl. ................................. 401/88; 401/201; 401/200; 53/437; 53/438; 53/526
[58] Field of Search .............. 264/69, 71, 266, 259; 401/200, 201, 88; 132/320; 15/104.93, 104.94; 141/69, 71, 110, 111, 114; 53/438, 437, 525, 526, 529, 528

[56] References Cited

U.S. PATENT DOCUMENTS

| | | | |
|---|---|---|---|
| 1,868,399 | 7/1932 | Slezak | 401/88 X |
| 2,175,133 | 10/1939 | Singleton | 401/88 X |
| 2,509,631 | 5/1950 | Dyer | 401/88 X |
| 2,800,673 | 7/1957 | Luzisky | 401/200 X |
| 3,463,302 | 8/1969 | Preston | 15/104.94 X |
| 3,717,427 | 2/1973 | Bodine | 264/71 X |
| 3,863,654 | 2/1975 | Morane et al. | |
| 4,938,952 | 7/1990 | Kamen et al. | |
| 4,962,627 | 10/1990 | Gueret | |
| 5,031,647 | 7/1991 | Seidler | 132/320 |

FOREIGN PATENT DOCUMENTS 0123766 11/1984 European Pat. Off. .
0310472 4/1989 European Pat. Off. .
2168625 1/1972 France .

OTHER PUBLICATIONS

Patent Abstract of Japan No. 1-151507, Jun. 14, 1989.
Patent Abstract of Japan No. 63-275511, Nov. 14, 1988.

Primary Examiner—Danton D. DeMille
Attorney, Agent, or Firm—Cushman, Darby & Cushman

[57] ABSTRACT

Process for compacting a pulverulent mixture (P) on a support (2) in order to obtain an applicator formed by the said support (2) provided with a pellet (23) of the compacted pulverulent mixture. Compacting is effected in an enclosure (11) in which a piston (3) slides, the piston (3) applying pressure to a layer of powder disposed at the bottom of the enclosure (11) and ultrasonic waves being emitted through the support (2) while the pressure is applied by the piston. The support (2) is provided with anfractuosities over at least part of its surface in contact with the pulverulent mixture.

13 Claims, 1 Drawing Sheet

PROCESS FOR COMPACTING A PULVERULENT MIXTURE ON A SUPPORT AND MAKE-UP APPLICATOR FORMED BY A SUPPORT PROVIDED WITH A PELLET OF COMPACTED PULVERULENT MIXTURE

This invention relates to a process for compacting a pulverulent mixture on a support and a make-up applicator formed by the support provided with a pellet of compacted pulverulent mixture obtained by this process.

French Patent Application 90 09327 filed on Jul. 20, 1990 by the Applicant describes a process for compacting a pulverulent mixture, in which a layer of pulverulent mixture is deposited at the bottom of an enclosure, a piston slides into this enclosure and applies pressure directly to the pulverulent mixture and, during the application of this pressure, the pulverulent mixture is subjected to the action of ultrasonic waves. According to the abovementioned application, the pulverulent mixture contains 5 to 80% of at least one thermoplastic pulverulent product, the remainder being formed by at least one non-thermoplastic product. The presence of a thermoplastic pulverulent product in the mixture to be compacted means that, as a result of the action of the ultrasonic waves, an inner and/or outer coating can be created in the pulverulent mixture, said coating holding the nonthermoplastic product.

The applicant has attempted to use this process to prepare applicators, more particularly applicators of small dimensions used as samples, by compacting the pulverulent mixture on a support. It has been noted that although the presence of the thermoplastic substance allowed the compacted mixture to be fixed to the support, the crumbling of the compacted mixture was not satisfactory. The only method of increasing the quantity of crumbling powder was to increase the thickness of the layer of mixture compacted on the support However, the thickness required to obtain a satisfactory crumbling fraction then gives the applicator an unattractive appearance and results in a loss of product as the crumbling fraction is small with respect to the entire compacted layer.

It was therefore desirable to find a process for fixing the compacted mixture to a support in which it is not necessary to apply an extremely thick layer of powder to the said support.

According to this invention, it has been found that this problem can be solved by using a support having anfractuosities (i.e., in particular, small cavities, pores, cells, irregularities, hairs or fibres), at least on the surface in contact with the pulverulent mixture, and by applying the pressure and ultrasonic waves to the mixture to be compacted through the support.

The first object of this invention is consequently a process for compacting a pulverulent mixture on a support, according to which a layer of pulverulent mixture to be compacted is deposited at the bottom of an enclosure, pressure is applied to the mixture to be compacted with the aid of a piston sliding in this enclosure and, simultaneously, ultrasonic waves are applied to the said mixture, characterised in that a support is placed on the layer of pulverulent material, at least the surface of said support in contact with the pulverulent mixture displaying anfractuosities, and that the pressure and ultrasonic waves are applied to the pulverulent mixture through the support.

It has been noted that with this process, if there is no thermoplastic product, the pulverulent mixture is fixed in a satisfactory manner to the support and the compacted pulverulent mixture crumbles in a suitable manner.

The pulverulent mixture consists of any mineral or inorganic product or any mixture of these products capable of being compacted under the operating conditions It consists more particularly of a product(s) intended for making up, e.g. the skin of the face or the eyelids Examples of mineral products are talc, clays, especially kaolin, mica and mineral pigments, e.g. titanium, zinc or iron oxides Examples of organic products are vegetable powders, such as rice starch or silk powder, non-thermoplastic polymer powders, such as polyacrylates, and fibres, e.g. cotton fibres.

A small quantity of thermoplastic product may also be introduced into the mixture to be compacted in order to improve the cohesion of the mixture after compacting. This quantity is advantageously less than 5%.

As explained hereinabove, the term "anfractuosities" refers to small cavities, pores, cells, irregularities, unevenness, or spaces between the hairs or fibres. These anfractuosities are obtained by using open-cell or semi-open-cell plastic foam supports, cellulose foam supports, compressed cotton supports or non-woven material supports. It is also possible to use supports covered on at least one face with flocking or a layer of foam. In this case, the support is preferably made of rigid or semi-rigid non-thermofusible plastic or of cardboard.

However, it is possible to use flocked foams or flocked nonwoven materials. Flocking is effected in the known manner by sticking threads or hairs made of, e.g. rayon, cotton, acrylic or polyamide resin on to the support with the aid of a varnish.

The anfractuosities preferably have dimensions greater than the diameter of the grains of the pulverulent mixture.

It may be supposed that in the course of compacting, the pulverulent mixture adheres to certain zones of the support as the ultrasonic waves disperse the powder in the anfractuosities formed, e.g. by the cells of the foams or the spaces between the fibres of the flocking.

The supports may have very variable shapes, such as narrow strips, or circular or oval plates which may or may not be provided with a shaft or handle for gripping the applicator.

According to one feature of the process of this invention, the pressure and ultrasonic waves are applied to the pulverulent mixture through the support. This gives more homogeneous compacting than when the pressure and ultrasonic waves are applied directly to the pulverulent mixture. Moreover, the compacting enclosure has a simple design, so that it is possible to produce applicators of different shapes.

The ultrasonic waves used according to the invention advantageously have a frequency of between 10 and 100 kHz and an amplitude of between 20 and 60 $\mu$m, the power delivered to the pulverulent mixture in the course of compacting being between 1 and 3 kw per $cm^3$ of compacted mixture. The emission time of the ultrasonic waves is between 0.25 and 3 s.

The pressure applied is preferably between $60 \times 10^5$ and $100 \times 10^5$ Pascals.

The piston applied to the support to effect compacting is advantageously formed by the sonotrode of an ultrasonic generator.

The enclosure generally consists of two superimposed parts, an upper part situated on the side of the opening of the enclosure having, in plan view, the shape of the support and a lower part situated on the side of the bottom of the enclosure having, in plan view, the shape it is desired to give the compacted pellet of pulverulent material. The bottom of the enclosure may be planar, concave or convex. It may also be provided with raised or recessed decorative patterns.

A layer of elastomer material, e.g. silicone, can be deposited at the bottom of the enclosure. A grating can also be placed at the bottom of the enclosure, on which the pulverulent mixture will be placed and which will serve as a vent during compression.

The end face of the piston can be planar, concave or convex.

According to a particular embodiment of the process according to the invention, the support is disposed with its packing on the bottom of the compacting enclosure, the pulverulent mixture to be compacted being placed between the said packing and the said support, the packing having a shape such that the piston can press against the part of the face of the support opposite that in contact with the pulverulent mixture to be compacted.

The second object of this invention is an applicator obtained by the process according to the invention, formed by a support provided with at least one pellet of compacted pulverulent material.

According to the invention, the support can be provided with one or more pellets. In the latter case, the applicator may consist of a palette of compacted products of different colours.

According to the invention, the support advantageously has anfractuosities over its entire outer surface, the pellet of compacted pulverulent material being disposed at right angles with part of the said anfractuosities. E.g. the support consists entirely of a foam or consists entirely of compressed cotton or consists of a completely flocked support or a support completely covered in foam. In all of these cases, one face of the applicator can be used for the application of the make-up powder and the other face can be used to blend in the make-up applied.

The applicator according to the invention is preferably protected by a packing. The applicator can be inserted into the packing before or after compacting of the pulverulent mixture. The packing may consist of a shell of injection moulded or moulded thermoplastic material or composite of solid fibre board cut to size containing the applicator and closed on its two faces by two covers, which may be transparent, at least one of which can be peeled off.

The invention will be more readily understood from the following description of one embodiment of the invention given by way of a non-limiting example and with reference to the accompanying drawings, in which.

Figure 1:
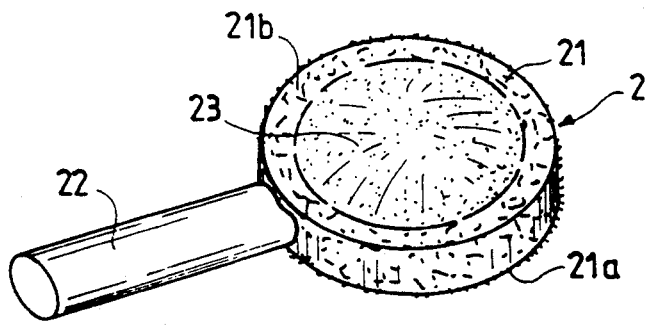
FIG. 1 is a perspective view of an applicator according to the invention.
Figure 2:
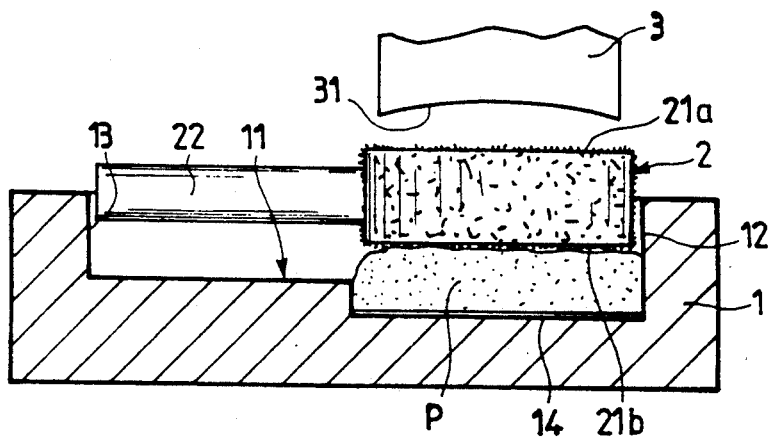
FIG. 2 is a vertical section of the compacting enclosure prior to compacting.
Figure 3:
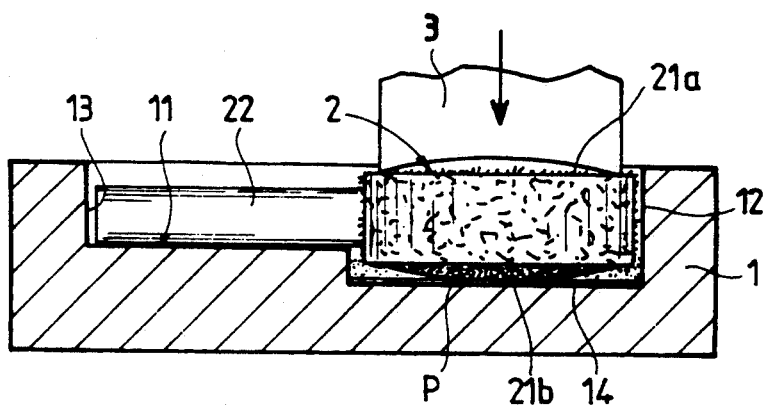
FIG. 3 shows the same enclosure after compacting.
Figure 4:
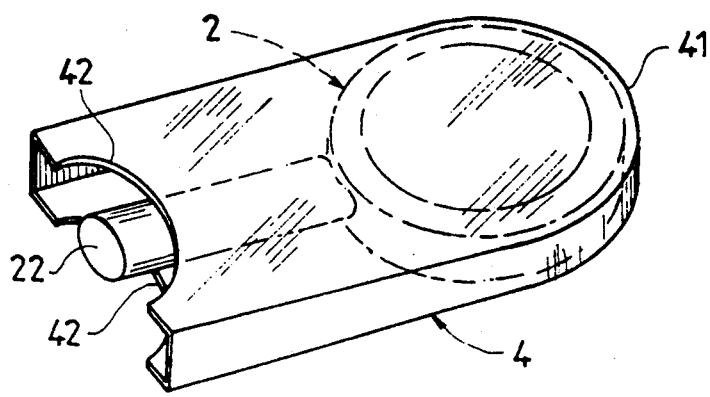
FIG. 4 shows the applicator of FIG. 1 in a protective packing.

As shown in FIGS. 2 and 3, in order to effect compacting, a layer of pulverulent mixture P and a support 2 are introduced into a mould 1. Pressure is then applied to the pulverulent mixture P through the support 2 with the aid of a piston 3 formed by the sonotrode of an ultrasonic generator.

In the embodiment shown, the support is in the form of a disc-shaped palette 21 provided with a handle for gripping the support. The palette 21 has a diameter of 8 mm and a thickness of 4 mm. It is completely flocked, i.e. on its two faces, with the aid of a rayon fibre flock having a length of 1 mm and a diameter of 0.06 mm.

An enclosure 11 open towards the top and divided into two parts 12 and 13 is formed in the mould 1. The lower part 12 situated on the side of the bottom 14 has the shape and dimensions, except for the necessary clearance, of the palette 21, and the upper part 13 has the shape of the entire support 2, i.e. the palette 21 and the handle 22. The enclosure has a diameter of 10 mm in the part 12 and a depth of 4 mm in the deepest part. The bottom 14 of the enclosure is planar.

In order to effect compacting, 0.2 ml of non-thermoplastic pigmentary powder containing 4% of magnesium stearate as a binder is introduced into the bottom 14 of the enclosure. The sonotrode 3 is then lowered until it is in contact with the upper face 21a of the support 2. A pressure of $60 \times 10^5$ Pascals is applied to the said support 2 by means of the sonotrode for 2.5 s. During compression, the sonotrode emits ultrasonic waves for 2 s, the power delivered in the form of ultrasonic waves during compacting being 2 kw/cm$^3$. The end 31 of the sonotrode 3 pressing against the support 2 is concave. This gives a pellet 23 of pulverulent mixture which is fixed to the lower face 21b of the palette 21. As the surface 31 of the sonotrode 3 is concave, the cohesion of the powder is greater at the periphery of the pellet 23 than in the centre. It has been measured that 90% by weight of the compacted pulverulent mixture forming the pellet 23 can crumble.

In order to protect the applicator, it is inserted into a packing 4 formed by a box substantially in the shape of a rectangular parallelepiped, one of the small sides of which is open and the other small side of which forms a semi-cylinder 41 having the same diameter, except for the necessary clearance, as the palette 21. The total length of the box is slightly greater than the largest dimension of the applicator 2, i.e. the total of the length of the handle 22 and the diameter of the palette 21. The thickness of the box is equal, except for the necessary clearance, to the thickness of the palette 21, including the thickness of the compacted pellet 23 of pulverulent mixture. The large faces of the parallelepiped are provided on the open side with notches 42 allowing the user to grip the handle 22 to remove the applicator 2.

When the user wishes to use the applicator 2 to apply make-up with the aid of the pulverulent mixture, he removes it from the packing 4 gripping it by the handle 22. He then applies the pulverulent mixture to the skin or the eyelids, rubbing the face 21b of the applicator provided with the pellet 23 over the skin in order to effect crumbling thereof. He then uses the face 21a of the applicator to blend in the make-up. The applicator is thrown away after use.

What is claimed is:

1. Process for compacting a pulverulent mixture (P) on a support (2), in which a layer of pulverulent mixture to be compacted is deposited at the bottom of an enclosure (11), a piston (3) slides in the enclosure, pressure is applied to the mixture to be compacted with the aid of a piston sliding in this enclosure and, simultaneously, ultrasonic waves are applied to the said mixture, characterised in that a support (2) is placed on the layer of pulverulent material to be compacted, at least the surface (21b) of said support in contact with the pulverulent mixture displaying anfractuosities, and that the pressure and ultrasonic waves are applied to the pulverulent mixture through the support (2).

2. Process according to claim 1, characterised in that the mixture to be compacted consists of a thermoplastic powder in a quantity of less than 5%.

3. Process according to one of claims 1 and 2, characterised in that an open-cell or semi-open-cell plastic foam support, a cellulose foam support, a compressed cotton support or a non-woven material support is used.

4. Process according to one of claims 1 and 2, characterised in that a rigid or semi-rigid support (2) of non-thermofusible plastic or of cardboard, at least partially flocked or covered with a layer of foam, or a support of flocked foam or non-woven material is used.

5. Process according to claim 4, characterised in that the anfractuosities have dimensions greater than the diameter of the grains of the pulverulent mixture.

6. Process according to claims 5, characterised in that the ultrasonic waves used have a frequency of between 10 and 100 kHz and an amplitude of between 20 and 60 $\mu$m, the power delivered to the pulverulent mixture in the course of compacting being between 1 and 3 kw per $cm^3$ of compacted mixture.

7. Process according to claim 6, characterised in that the emission time of the ultrasonic waves is between 0.25 and 3 s.

8. Process according to claim 7, characterised in that the pressure applied during the ultrasonic emission is between $60 \times 10^5$ and $100 \times 10^5$ Pascals.

9. Process according to claim 8, characterised in that the piston applied to the support to effect compacting is formed by the sonotrode of an ultrasonic generator.

10. Process according to claim 9, characterised in that a layer of elastomer material is deposited at the bottom of the enclosure.

11. Process according to claim 10, characterised in that a grating is placed at the bottom of the enclosure.

12. Process according to claim 11, characterised in that the support is disposed with its packing on the bottom (14) of the compacting enclosure (11), the pulverulent mixture to be compacted being placed between the said packing and the said support and the packing having a shape such that the piston can press against the part of the face of the support opposite that in contact with the pulverulent mixture to be compacted.

13. Applicator obtained by the process according to claim 12, formed by a support provided with at least one pellet of compacted pulverulent material.

* * * * *